United States Patent [19]

Barkan

[11] Patent Number: Plant 5,442

[45] Date of Patent: Apr. 23, 1985

[54] AVOCADO TREE-SCHILLER

[75] Inventor: Pinchas Barkan, Kvutsat Schiller, Israel

[73] Assignee: Kvutsat Schiller Kvutsat Ovdim Lehityashvut Shitufit Ltd., Kvutsat Schiller, Israel

[21] Appl. No.: 510,751

[22] Filed: Jul. 1, 1983

[51] Int. Cl.[3] ..... A01H 5/03

[52] U.S. Cl. ..... Plt./44

[58] Field of Search ..... Plt./44

*Primary Examiner*—Robert E. Bagwill

*Attorney, Agent, or Firm*—Browdy and Neimark

[57] ABSTRACT

A new variety of avocado tree of the Mexican group. This new variety is distinctive in that the fruit ripens early for a Mexican group avocado tree. The new variety produces fruit which is larger and more oval than fruit from other Mexican varieties and which has light green skin on maturity, as compared to other Mexican varieties whose skins turn purple.

1 Drawing Figure

DESCRIPTION OF THE NEW VARIETY

This invention relates to a new variety of avocado tree, which is of the species *Persea americane,* falling within the group of Mexican avocados, grown from seed in the orchard of Kibbutz Kvutsat Schiller, Israel. The characteristics hereafter described will be such as have been observed in trees grown in that geographical region.

The new variety was asexually reproduced by grafting onto rootstock Nahalat 9 as well as onto rootstock of itself. The characteristics of the new variety are reproduced in stock similarly grafted or grafted onto any other suitable avocado root stock. The new variety is useful both for providing fresh fruit for consumption and as rootstock.

DESCRIPTION OF THE DRAWINGS

The drawings illustrate typical fruit and foliage of the new variety.

THE TREE

The avocado tree, whose proposed denomination is "Schiller", is of the erect-wide growth type. It has an erect trunk with branches spreading outward and upward. During three years of study, it has been found that the variety is productive but the trees are somewhat irregular bearers, in that the yield of fruit varies from year to year.

The bark of the tree is smooth and without cracks.

FOLIAGE

The young shoot of the tree has a leaf which is green-brown in color and has many red lenticels on its branch. There is no pigment in the young leaf. The mature leaf has a dark green upper side, about Yellow Green Group 147 A in The Royal Horticultural Society Colour Chart, similar to that of the Etinger and Fuerta varieties, and a strong anise fragrance.

The blade of the leaf is of medium length and narrow width as compared with leaves of other Mexican varieties. It has a base which describes a right or obtuse angle and a distal portion describing an acute angle. A lengthwise cross section of the leaf blade is concave in shape, and a widthwise cross section is flat in shape. The margin of the leaf has some waviness.

The tree begins to flower in mid-February and its blooming season ends about mid-April. This flowering time is earlier than most varieties, including the Fuerta variety which, itself, flowers relatively early, and flowering is of medium duration, i.e., about two months. The intensity of flowering is intermediate, as compared with the Fuerta variety.

The peduncle is short compared with the Etinger variety, i.e., less than 5 cm. in length. The flowers fall into the "B" group which open on one afternoon as female flowers (i.e., with a mature pistil) and open again as masculine flowers (i.e., with mature stamens) in the morning two days later.

FRUIT

The tree sets fruit beginning in February and extending through April. The fruit is ripe for picking from the middle of September through the middle of October. Ripe for picking as used herein means edible, which is generally at the time when the oil content of the avocado reaches approximately 8%. It is a particular feature of the present variety of avocado that its fruit both appears and ripens relatively rapidly. Thus, a relatively short time is required between blossoming of the flowers and harvesting of the fruit. In Israel, for example, six months after flowering, the fruit is mature for picking. This is two weeks earlier than other early commercial varieties in the same geographical area.

The avocado fruit produced is generally oval without a pronounced neck, that is, rounded at the base and narrowing slightly towards the stem. It is of medium length, generally ranging between 10 and 12.3 centimeters, and of medium diameter, generally averaging between 5.8 and 6.8 centimeters. The ratio of length to diameter is about 1.77. The average weight is in the range of 200 to 320 grams.

The length of the fruit stalk, up to the first node, is medium to short, about 12 mm. The stalk is positioned obliquely in the fruit, and most fruit of this variety is slightly curved-in opposite the stem.

The mature fruit has a very thin, somewhat glossy, light green skin, of color 147-A,B of the Yellow Green Group in The Royal Horticultural Society Colour Chart, with non-conspicuous lenticels. This is unusual in a variety of Mexican avocado since the skins of their fruit generally turn purple on maturity.

The skin surface has a smooth texture with no blistering and no ribs. The skin is very thin and leathery, i.e., it is flexible and does not break into pieces, so it is easy to peel from the flesh.

The seed of the avocado is essentially almond shaped and slightly offset at the tip. The seed cavity is of diameter between 28 and 35 mm. The seed ranges between 50–63 mm in length, 28–35 mm in diameter and 24–33 grams in weight. The seed coat is loose and the seed adheres somewhat than to the flesh.

The flesh of the mature fruit is smooth with no discernible fibers. The color of the flesh of the mature fruit near the seed is light yellow, about 4C Primrose Yellow in The Royal Horticultural Society Colour Chart, varying to yellow-green adjacent the outer skin.

The flesh has a buttery texture and a nutty flavor without bitterness. It has a slight aroma and tends to blacken when exposed to air.

I claim:

1. The new variety of avocado tree of the Mexican group substantially as described and illustrated herein, being distinguished for its ability to produce mature fruit having light green skin and to bring this fruit to maturity about two weeks earlier than the fruit of comparable early maturing avocado varieties in the same growing area.

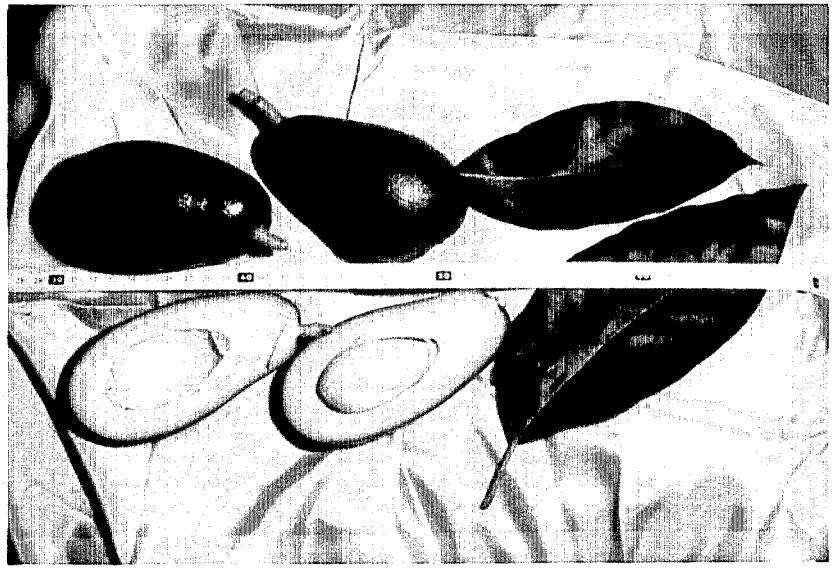

* * * * *